US00PP11001P

United States Patent [19]

Spaans

[11] Patent Number: Plant 11,001

[45] Date of Patent: Jul. 6, 1999

[54] VARIETY OF CALLA LILY PLANT NAMED 'SCHWARZWALDER'

[75] Inventor: Jaap P. Spaans, Alkmaar, Netherlands

[73] Assignee: Sande BV, Netherlands

[21] Appl. No.: 08/918,659

[22] Filed: Aug. 22, 1997

[51] Int. Cl.[6] ..... A01H 5/00

[52] U.S. Cl. ..... Plt./263

[58] Field of Search ..... Plt./68.1, 263

[56] References Cited

PUBLICATIONS

UPOV–ROM, 1998/01, Plant Variety Database, GTI Jouve Retrieval Software, citations for 'Schwarzwalder'.

*Primary Examiner*—Howard J. Locker
*Attorney, Agent, or Firm*—Webb Ziesenheim Logsdon Orkin Hanson, P.C.

[57] ABSTRACT

Schwarzwalder is a new variety of calla lily having a flower with a deep purple colored spathe and deep purple colored spadix and producing 2–7 flowers per tuber. The leaves are medium green with whitish spots and have a leathery texture.

2 Drawing Sheets

BACKGROUND OF THE NEW PLANT

The present invention comprises a new and distinct cultivar of calla lily, botanically known as *Zantedeschia sprengeri* and hereinafter referred to by the cultivar name Schwarzwalder.

Schwarzwalder is a product of a planned breeding program which had the objective of creating Zantedeschia hybrids for cut flower production in a wide range of colors with a large, classic flower shape. The breeding program began in 1989 and the new cultivar is a seedling selected from the crossing of a *Zantedeschia sprengeri* variety known as 'Pacific Pink' with a mixture of pollen from unknown parentage. Schwarzwalder was originated in 1990 by the inventor Jaap. P. Spaans in 't Zand, The Netherlands as one flowering plant within the progeny of the stated cross.

The first act of asexual reproduction of Schwarzwalder by tissue culture was performed by the inventor in August 1992 in 't Zand, The Netherlands. Subsequent asexual reproduction by tissue culture at the same location has demonstrated that the combination of characteristics as herein disclosed for the new cultivar are retained through successive generations of asexual reproduction.

The following observations, measurements and comparisons describe plants grown in 't Zand, The Netherlands under greenhouse conditions which approximate those generally used in horticultural practice. Color references are made to the R.H.S. Colour Chart of The Royal Horticultural Society of London, except where general color terms of ordinary significance are used.

The following traits have been repeatedly observed and determined to be basic characteristics of Schwarzwalder which, in combination, distinguish this calla lily as a new and distinct cultivar:

1. Deep purple spathe
2. Purple spadix
3. Two flowers per tuber of 9–12 cm in circumference; 2–5 flowers per tuber of 12–15 cm in circumference; and 4–7 flowers per tuber of 15–18 cm in circumference.

BRIEF DESCRIPTION OF THE DRAWINGS

The accompanying photographic drawings illustrate the new variety, with the colors being as nearly true as is possible with color illustrations of this type.

DESCRIPTION OF THE NEW PLANT

The Plant

Figure 1:
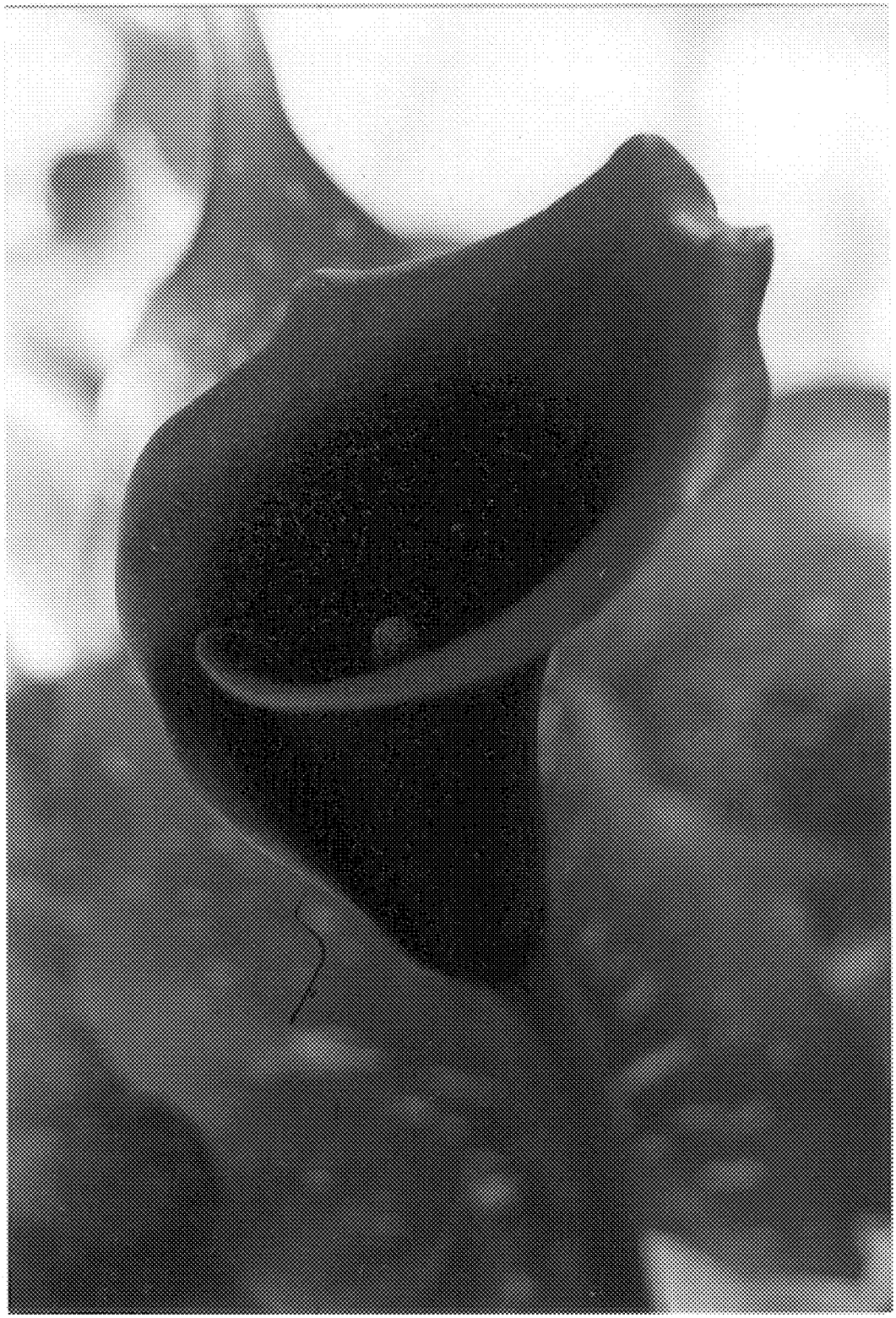
FIG. 1 is a photograph of the flower of Schwarzwalder.
Figure 2:
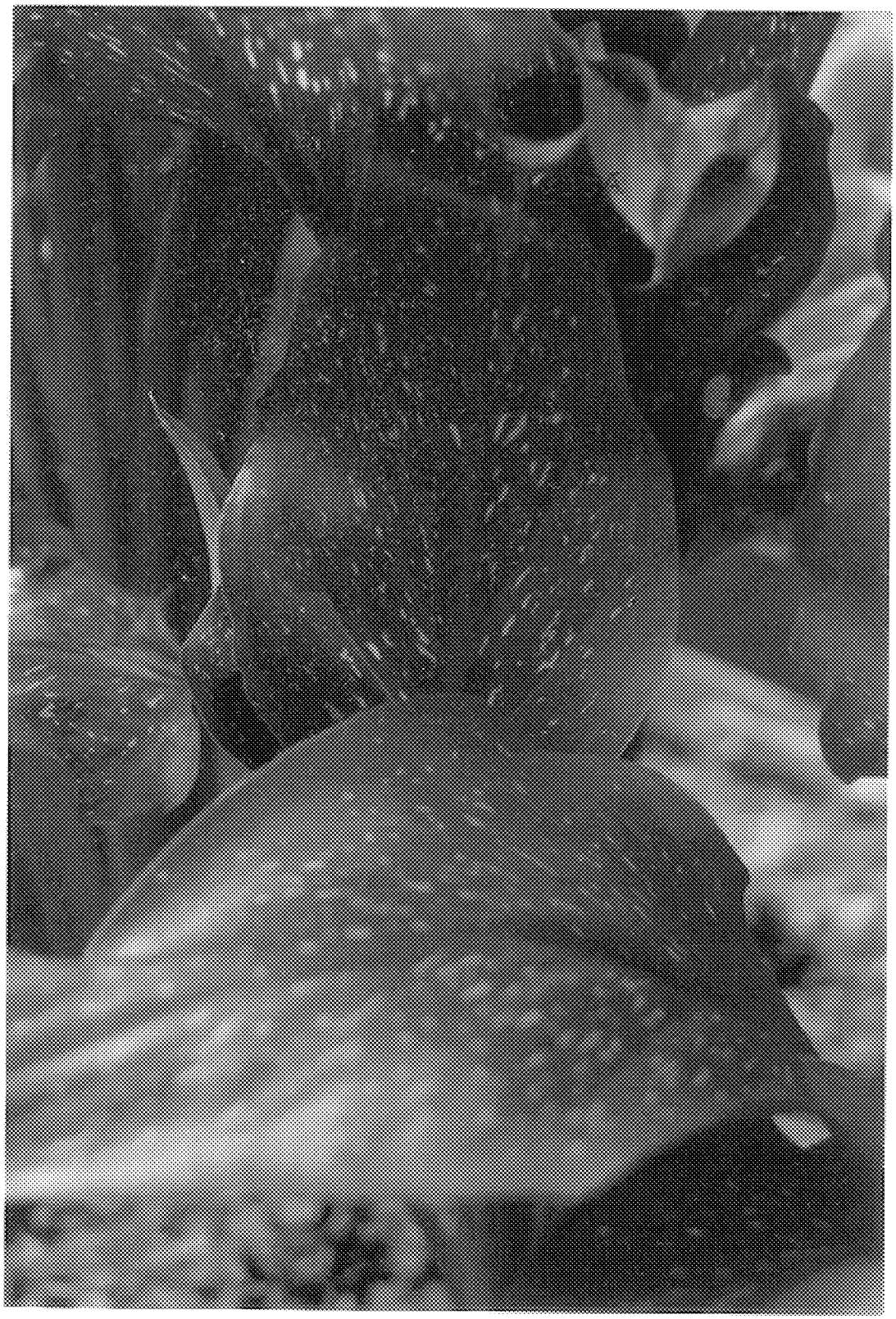
FIG. 2 is a photograph of the leaves of the Schwarzwalder plant.

Size:
- *Height of leaf canopy above soil.*—50–65 cm.
- *Height of top of flowers above soil.*—60–75 cm.
- *Diameter.*—30–40 cm.

Form: Erect.

Number of flowers per tuber:
- *Tuber circumference of* 9–12 *cm.*—2 flowers.
- *Tuber circumference of* 12–15 *cm.*—2–5 flowers.
- *Tuber circumference of* 15–18 *cm.*—4–7 flowers.

Branches:
- *Character.*—Strong.
- *Color.*—Yellow-Green Group 144C.
- *Number per plant.*—3.

Leaves:
- *Size.*—Width: 10–14 cm. Length: 25–35 cm. Shape: Elliptic.
- *Number per plant.*—10 .
- *Color.*—Upper surface: Green Group 143A with transparent spots having edges of White Group 155D. Lower surface: Green Group 143C.
- *Margin.*—Slightly wavy.
- *Veins.*—Configuration: Pinnate. Color: Yellow-Green Group 144B.
- *Surface quality.*—Leathery.
- *Petiole.*—Length: 25–30 cm. Color: Yellow-Green Group 144C.

Roots:
- *Color.*—White.
- *Branching.*—Average amount.

The Flower

Spathe:
- *Size.*—Length: 8–11 cm. Width: 5–6 cm.
- *Color.*—Upper surface: Greyed-Purple Group 187A. Lower surface: Varies between Greyed-Purple Group 187A and Black Group 202A.

*Veins*.—Color: Varies between Greyed-Purple Group 187A and Greyed-Purple Group 187B.

*Shape*.—Cupped.

Spadix:

*Size*.—Length: 50-55 mm.

*Color*.—Varies between Greyed-Purple Group 185A and Greyed-Purple Group 187B.

*Position relative to spathe*.—Upright.

Peduncle:

*Size*.—Length: 55–65 cm. Diameter: 9–11 mm.

*Color*.—Varies between Green Group 143C and Yellow-Green Group 144C.

Reproductive organs:

*Location of female organs*.—Basal portion of the spadix.

*Location of male organs*.—Upper portion of the spadix.

*Perianth*.—Conspicuous.

*Stamens*.—Not visible before pollen release.

*Pistil*.—Length beyond perianth: About 1 mm.

Disease resistance: No unusual susceptibility to disease.

Pest resistance: No unusual susceptibility to pests.

Flowering: Tubers planted in a greenhouse in The Netherlands in February produce flowers in April. Tubers planted outdoors in The Netherlands in May produce flowers in July.

Lastingness: About 3 weeks on the plant.

Fragrance: None.

I claim:

1. A new and distinct variety of calla lily plant named 'Schwarzwalder' as described and illustrated.

* * * * *